United States Patent [19]

Hadaway et al.

[11] Patent Number: 5,296,234
[45] Date of Patent: Mar. 22, 1994

[54] HOLDER AND PACKAGING FOR A HARDENED MEDICATED MATRIX

[75] Inventors: Michelle A. Hadaway, Gurnee; David E. Kramer, Northbrook; Robert J. Best, Winthrop Harbor, all of Ill.

[73] Assignee: Abbott Laboratories, Abbott Park, Ill.

[21] Appl. No.: 776,543

[22] Filed: Oct. 11, 1991

[51] Int. Cl.$^5$ .............................................. A61K 9/14
[52] U.S. Cl. ..................................... 424/484; 424/440
[58] Field of Search ................ 424/484, 440; 514/317, 514/777

[56] References Cited

U.S. PATENT DOCUMENTS

| | | | |
|---|---|---|---|
| 4,671,953 | 6/1987 | Stanley | 514/777 |
| 5,132,114 | 7/1992 | Stanley | 424/440 |

Primary Examiner—Thurman K. Page
Assistant Examiner—William E. Benston, Jr.
Attorney, Agent, or Firm—Thomas M. Breininger

[57] ABSTRACT

A stick-like holder and packaging, including an overcap and a sealed, light, moisture and tamper resistant foil pouch, for a hardened, medicated matrix affixed to one end of the holder including detent means for releaseably mounting the overcap on the matrix end of the holder and with the holder having a flat, label receiving handle at its other end and a flange to prevent swallowing of the holder when placed in a patient's mouth to medicate or pre-medicate the patient.

12 Claims, 3 Drawing Sheets

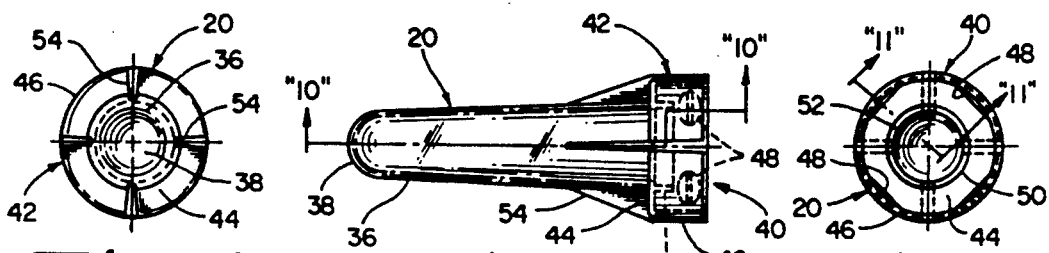
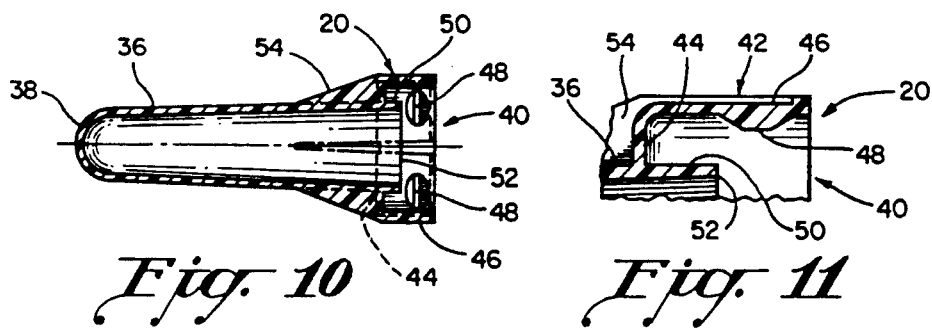
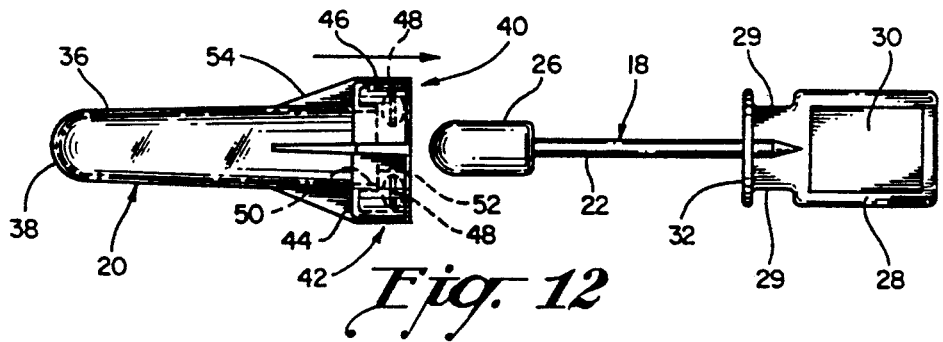

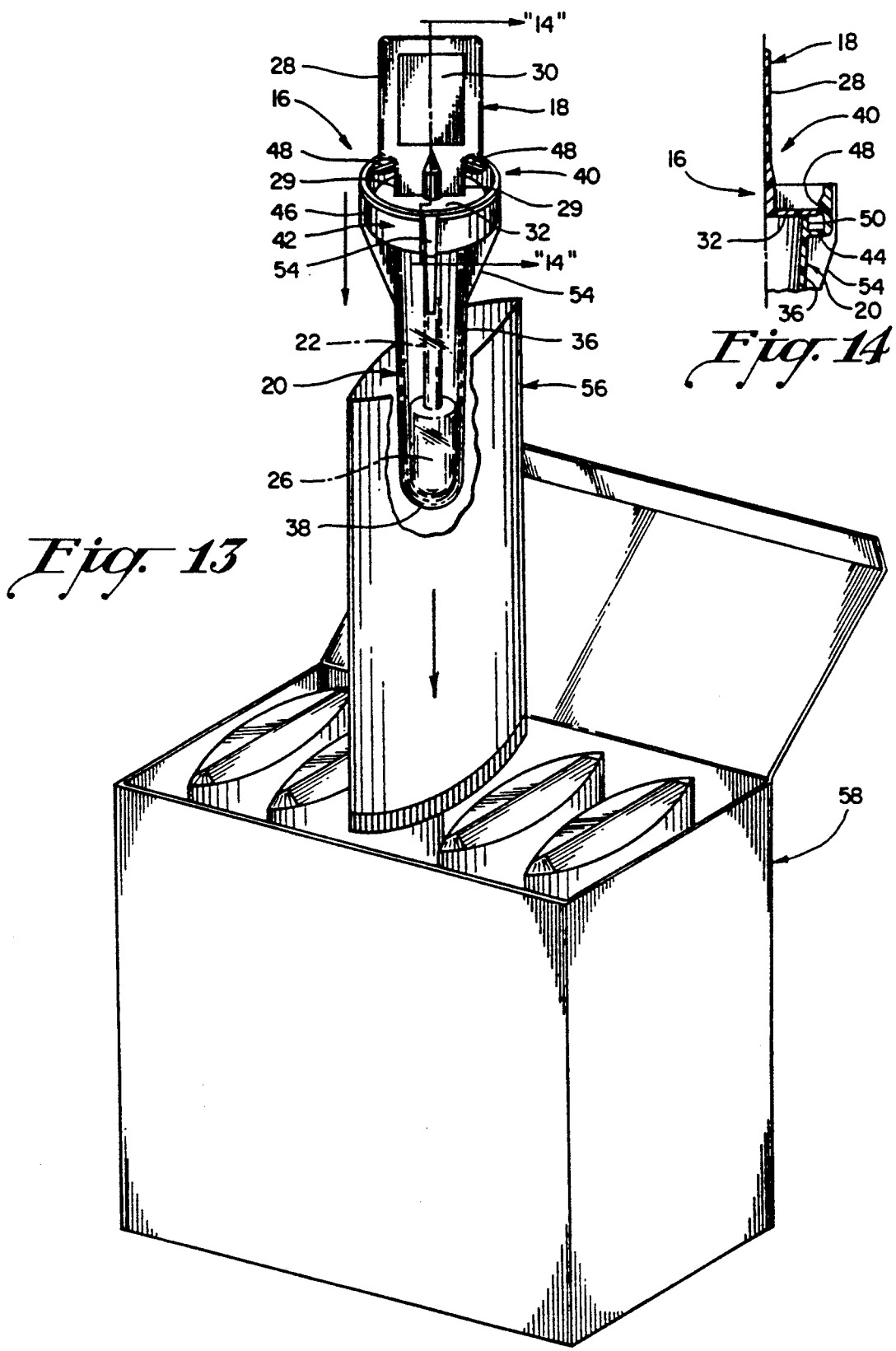

HOLDER AND PACKAGING FOR A HARDENED MEDICATED MATRIX

A recent development in the health care field, particularly related to the administration of medication, is the formulation of some medications in a pleasant-tasting hardened matrix. The desired dosage can accurately be controlled and accounted for and there is no likelihood of spillage, as when administering liquid medications to babies, children and elderly persons, whereupon the dosage received may be less than the dosage prescribed.

This medicated matrix may be formed on the end of a stick to provide a product which is particularly well-adapted for administrating certain medications to elderly persons and others who are emaciated and weakened by their illnesses and who, therefore, are often very difficult to medicate by injection or even orally as they often have difficulty in swallowing pills and the like. Likewise, such a product is a natural for administering medications to young people and children.

One hardened, sucrose based, medicated matrix product of the type discussed hereinbefore is disclosed in U.S. Pat. No. 4,671,953 which is incorporated herein by reference. Whereas the foregoing U.S. Pat. No. 4,671,953 discusses use of a simple stick upon which the medicated matrix may be formed, no specific stick structure or packaging arrangement is shown or described.

SUMMARY OF THE INVENTION

The present invention is directed to a new, novel and improved stick-like holder for such products having safety and other features not previously disclosed and also to a new and novel pack-up or packaging arrangement for such products.

This product, which is characterized, in part, by a sucrose based hardened matrix containing a dosage of medication, such as fentanyl citrate, which is mounted on the end of an elongated stick-like holder having a handle portion at its opposite end, provides a non-invasive means for achieving analgesia, sedation and relief from anxiety through transmuscosal absorbtion of the prescribed medication interspersed through the aforesaid hardened, pleasant-tasting "matrix on a stick" when same is placed in the mouth. It is particularly useful as a premedication before anesthesia, before a painful diagnostic procedure, for emergency room pain management, for post-operative pain control, etc.

The matrix holder has a comfortable handle which is also adapted to receive a pressure sensitive label carrying important information as to the medication dispersed through the matrix and is of a proper length so that the matrix end can comfortably reach the buchal pouch area of the mouth. Further, the handle is molded of a suitable plastic which has enough flexibility that it wouldn't splinter or crack if the patient should fall with the handle in his or her mouth. Another safety feature of the holder is an integral flange adjacent the handle which insures against the holder being swallowed.

The plastic overcap, which is an important part of the novel packaging arrangement, is in the form of a tubular member having a closed end and an open end for receiving therein the matrix-bearing end of the elongated handle. Detent means are provided for retaining the overcap on the handle during shelf storage and/or transporting of the product, between intermittent uses of same by the same patient, and to dispose of the unused portions of the product, particularly if the matrix medicament should be a "controlled substance". Although generally tubular or cylindrical, the overcap is provided with rib means which prevent free rolling of the matrix holder/overcap assembly when placed on a flat surface, as off a table or countertop.

Another part of the packaging arrangement is a foil pouch in which the matrix holder/overcap assembly is sealed, the laminated foil pouch being light, vapor, moisture, and tamper resistant. The pouch, which can also be labeled, cushions and provides good shelf life for the matrix holder/overcap subassembly.

An object of the present invention is to provide a new and improved stick-like holder for a hardened medicated matrix to be placed in a patient's mouth and a novel packaging arrangement therefor including on overcap and a foil pouch.

This and other objects and features of the present invention will become more fully apparent from the following description and appended claims taken in conjunction with the accompanying drawings.

BRIEF DESCRIPTION OF THE DRAWINGS

FIG. 7 is a side elevational view of the overcap shown in FIG. 1;

FIG. 8 is a left end elevational view thereof;

FIG. 9 is a right end elevational view thereof;

FIG. 10 is a longitudinal sectional view thereof taken generally along line 10—10 of FIG. 7;

FIG. 11 is an enlarged fragmentary sectional view thereof taken generally along line 11—11 of FIG. 9;

FIG. 12 is a side elevational view showing the beginning of the assembly of the overcap over the matrix-bearing end of the stick-like holder;

FIG. 13 is a perspective view illustrating a preferred embodiment of the packaging arrangement of the present invention including sealing receipt of the matrix holder/overcap assembly into the foil pouch and packing of several of the sealed pouches into a carton; and FIG. 14 is a fragmentary sectional view showing the detent interengagement means between the matrix holder and the overcap.

DESCRIPTION OF THE PREFERRED EMBODIMENT

Figure 1:
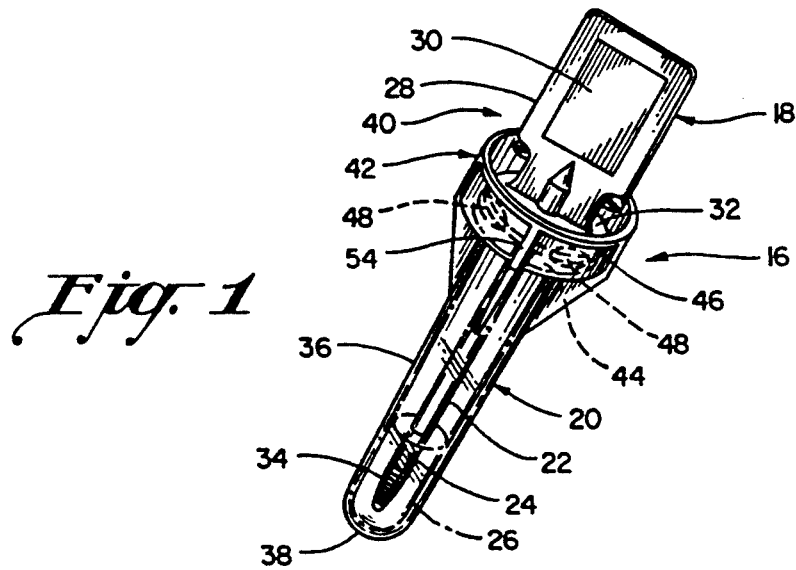
FIG. 1 is perspective view of an interengaged stick-like medicated matrix holder and an overcap therefor embodying a preferred embodiment of the invention.
Figures 2, 3, 4:
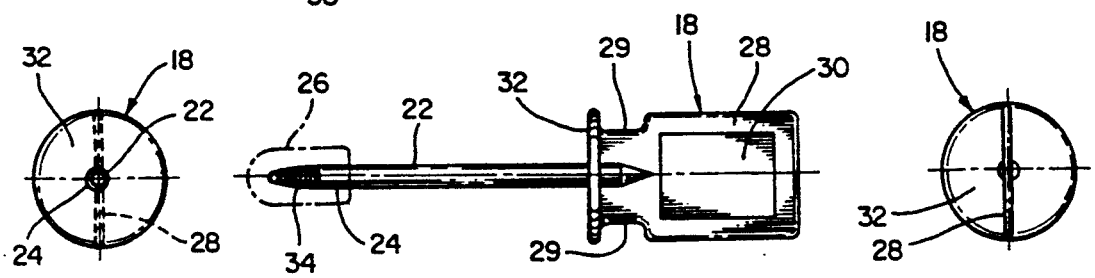
FIG. 2 is a side elevational view of the stick-like holder shown in FIG. 1 with the medicated matrix shown in broken line.
FIG. 3 is a left end elevational view thereof.
FIG. 4 is a right end elevational view thereof.
Figure 5:
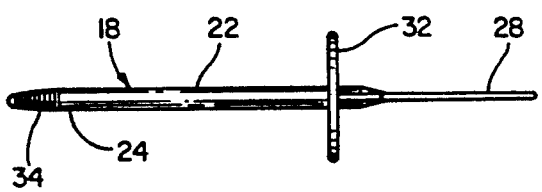
FIG. 5 is a top plan view thereof.

Referring now to the drawings, a preferred embodiment of a portion of the invention is shown in FIG. 1 in the form of an assembly or interengagement 16 of a stick-like holder 18 having a hardened, sucrose based medicated matrix 26 affixed to one end 24 thereof with a protective overcap 20. The stick-like holder 18 which is formed of a suitable plastic as a one-piece elongated element by an injection molding process, for instance, is characterized by a relatively thin, cylindrical rod-like member 22 having the medicated, but pleasant-tasting, matrix 26 affixed to the one end 24 thereof and a handle 28 at its opposite end. The handle 28 is flat for comfortable gripping and the length of the holder 18 is such that the medicated matrix 26 can easily be inserted into the patient's mouth and into the buchal pouch portion thereof for most effective transmucosal absorbtion of the medicament interspersed though the hardened matrix 26. As is illustrated in FIG. 2, the opposite side edges of the handle 28 are provided, adjacent a circular flange 32 on the holder 18, with cut-away portions 29.

Figure 6:
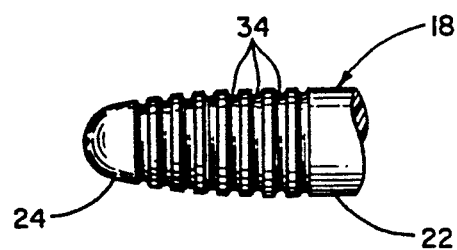
FIG. 6 is an enlarged fragmentary view of the matrix supporting end of the stick-like holder as circled in FIG. 5.

As previously noted herein, the medicated matrix 26 is particularly well suited as a premedication before anesthesia, before a painful diagnostic procedure, for emergency room pain management, for post-operative pain control, etc., thus providing a non-invasive procedure for achieving analgesia, sedation and relief from anxiety. As noted in U.S. Pat. No. 4,671,953 which is incorporated herein by reference, one suitable medicament for the medicated matrix 26 would be fentanyl citrate. A pressure sensitive mylar label 30 bearing informative data as to the medicated matrix 26 may be applied to one or both sides of the flat handle 28. As illustrated in FIG. 6, the matrix-bearing end 24 of the stick-like holder 18 is gently tapered toward a rounded end thereof and is provided with a longitudinally spaced series of annular rounded grooves 34 which serve to effectively affix the medicated matrix 26 thereto.

The elongated holder 18 is formed of a sufficiently flexible plastic that should a patient fall with the holder 18 in his or her mouth, the holder 18 will not splinter or crack. Another safety feature is the circular flange 32 which is integrally formed on the elongated holder 18 normally thereto and adjacent the cut-away portions 29 of the flat handle 28. This circular flange 32 prevents a patient from swallowing the elongated holder 18 and serves further purposes which will be described hereinafter.

The overcap 20, which may also be injection molded, is formed of plastic and is characterized by a generally tubular body portion 36 having a closed end 38 and an open end 40. The body portion 36 tapers slightly outwardly from the closed end 38 toward the open end 40 to facilitate removal of same from its mold. The open end 40 is provided with a generally cylindrical end portion or collar 42 which is defined by an outwardly projecting annular flange portion 44 and a cylindrical wall portion 46 which extends in an axial direction away from the closed end 38 at a right angle from the outer edge of said annular flange portion 44. The inner diameter of the cylindrical end portion 42 is slightly greater than the diameter of the circular flange 32 provided on the elongated holder 18. A series of four retaining bumps 48 are provided on the inner surface of the cylindrical end portion 42 in circumferentially spaced relationship and serve as part of detent means for releaseably interengaging the elongated matrix bearing holder 18 with the overcap 20, the other part of the detent means being the circular flange 32 on the elongated holder 18. The detent means is best illustrated in FIG. 14 which shows the edge of the circular flange 32 after same has been resiliently snapped past the retaining bumps 48 upon inserting the matrix bearing end 24 of the holder 18 into the open end 40 of the overcap 20, as shown in FIG. 12. Inward movement of the elongated holder 18 into the overcap 20, to prevent engagement of the medicated matrix 26 with the closed end 38 of the overcap 20, is limited by an integral concentric annular wall structure 50 which is disposed within the cylindrical end portion 42 with its outermost edge 52 being spaced inwardly of the outer edge of the cylindrical wall portion 46 and generally in alignment with the innermost portions of the retaining bumps 48. As shown in FIG. 14, once the circular flange 32 has been snapped over the retaining bumps 48 to releaseably interengage the matrix bearing holder 18 in the overcap 20, the flange 32 engages the annular wall structure 50 to limit further inward movement of the matrix bearing end 24 of the holder 18. The diameter of the annular wall structure 50 is less than that of the cylindrical wall portion 46 and the wall structure 50 generally defines an extension of the tubular body portion 36 of the overcap 20 longitudinally beyond the annular flange 44. The aforesaid structure of the collar 42 provides sufficient flexibility of the cylindrical wall portion 46 for effective operation of the detent means and insures that the holder 18 is always held tightly in the overcap 20 and doesn't rattle even if the tolerances are not met exactly.

The outer surface of the cylindrical end portion 46 and the adjacent outer surface of the tubular body portion 36 of the overcap 20 are provided with a circumferentially spaced series of four longitudinally disposed ribs 54. Should the interengaged holder 18 and overcap 20 be laid down on a flat surface such as a table or countertop, the ribs 54 prevent free rolling of the holder/overcap assembly 16 onto the floor, any rolling would be limited to less than 90°. So as to not detrimentally effect the aforesaid flexibility of the cylindrical wall portion 46, the ribs 54 are disposed between the retaining bumps 48 rather than in angular alignment therewith.

The preferred embodiment of the packaging arrangement further includes, as illustrated in FIG. 13, a laminated foil pouch 56 in which the holder/overcap assembly 16 is sealed prior to placing several of such sealed pouches 56 in a carton 58. The foil pouches 56 serve to cushion the handle/overcap assemblies 16 and, as the pouches 56 are light, moisture, and vapor proof, also provide good shelf life. The very nature of the pouches 56 provides clear evidence of any tampering therewith. Although not specifically illustrated, the pouches 56 may be imprinted with pertinent data or preprinted pressure sensitive labels may be applied thereto.

With reference again to the overcap 20, it is noted that same is very convenient for storing the matrix bearing holder 18 during intermittent use thereof by a patient and for return of an unused portion thereof to a hospital pharmacy, particularly if the medicament in the matrix 26 is a "controlled substance".

The one-piece elongated plastic holder 18 having a pleasant-tasting, hardened medicated matrix 26 affixed to one end thereof provides a non-invasive drug delivery means which is especially well-adapted for premedicating children and elderly patients, a safety flange 32 being provided so that the matrix bearing holder 18 can not be accidentally swallowed. When medicating a patient, the physician can observe when the desired anesthesia, sedative or analgesia effect has been achieved, at which point the matrix bearing holder 18 can be removed from patient's mouth. Further, more responsive patient's can use this drug delivery product to self-administer medication and thus to self-manage their very individual pain experience.

While there has been shown and described a preferred embodiment of the invention, it will be obvious to those skilled in the art that changes and modifications may be made without departing from the invention, and it is intended by the appended claims to cover all such changes and modifications as fall within the true spirit and scope of this invention.

We claim:

1. A stick holder and packaging for a hardened sucrose based matrix containing a dosage of fentanyl citrate comprising; a one-piece elongated molded plastic holder having a medicated hardened sucrose based matrix affixed to one end thereof wherein said one end of said elongated holder is provided with a series of longitudinally spaced annular rounded grooves for effectively affixing said hardened sucrose based medicated matrix to said one end of said holder, a handle portion at the opposite end thereof said handle portion being flat to facilitate gripping of same and to provide a surface upon which a pressure sensitive label may be applied, and a flange portion disposed perpendicular to said elongated holder adjacent the inner end of said handle portion; a molded plastic tubular overcap closed at one end and open at the opposite end and adapted to fit completely over said one end of said holder; and interengaging means for retaining said overcap on said one end of said holder.

2. The invention as defined in claim 1 wherein the open end of said overcap is generally cylindrical, said holder flange portion is circular and of a size whereby same is receivable within said generally cylindrical open end of said overcap, and wherein the inner surface of said open end of said overcap is provided with a series of circumferentially spaced retaining bumps over which the edge of said circular flange on said holder is snappable to retain said overcap on said holder, said circular flange and said retaining bumps defining said means for retaining said overcap on said one end of said holder.

3. The invention as defined in claim 2 wherein an integral annular concentric wall configuration is provided in said cylindrical open end of said overcap which is of smaller diameter and spaced longitudinally inwardly of the outer edge thereof and in general alignment with the innermost portion of said retaining bumps, the outer edge of said annular concentric wall configuration being engageable by said circular flange portion of said holder after the edges thereof have snapped over said retaining bumps during assembly of said overcap onto said one end of said holder whereby to limit inward movement of said holder into said overcap so as to prevent engagement of said hardened medicated matrix affixed to said one end of said holder with said closed end of said tubular overcap.

4. The invention as defined in claim 1 wherein said interengaged stick holder and overcap are sealed in a foil pouch which is light, moisture and tamper resistant.

5. A stick holder for a hardened medicated matrix comprising; a one-piece elongated molded plastic holder having a hardened medicated matrix affixed to one end thereof; a handle portion formed on the opposite end of said elongated holder; and a flange portion formed on said holder adjacent the inner end of said handle portion and disposed perpendicular to said elongated holder.

6. The invention as defined in claim 5 wherein said handle portion is flat to facilitate gripping of same and to provide a surface upon which a pressure sensitive label may be applied.

7. The invention as defined in claim 5 wherein said one end of said elongated holder is provided with a series of longitudinally spaced annular rounded grooves for effectively affixing said hardened medicated matrix to said one end of said holder.

8. The invention as defined in claim 5 wherein the medication in said medicated hardened matrix affixed to said one end of said one-piece elongated molded plastic holder is fentanyl citrate.

9. A stick holder and packaging for a hardened medicated matrix comprising; a one-piece elongated molded plastic holder having a medicated hardened matrix affixed to one end thereof, a flat handle portion at the opposite end thereof, and a circular flange portion disposed perpendicular to said elongated holder adjacent the inner end of said flat handle portion; a molded plastic tubular overcap closed at one end and open at the opposite end and adapted to fit over said one end of said holder; means for retaining said overcap on said one end of said holder in interengaged relationship therewith; and a foil pouch into which said interengaged holder and overcap are sealed, said pouch being light, moisture and tamper resistant.

10. The invention as defined in claim 9 wherein the open end of said tubular overcap is generally cylindrical in configuration and wherein a series of longitudinally disposed external ribs are circumferentially spaced about said generally cylindrical open end of said overcap to deter free rolling of said interengaged holder and overcap when laid on a flat surface.

11. The invention as defined in claim 10 wherein a series of circumferentially spaced retaining bumps are provided on the inner surface of said cylindrical open end of said overcap and spaced inwardly from the outer edge thereof, and wherein an integral annular concentric wall configuration is provided in said generally cylindrical open end of said overcap which is of a smaller diameter than said cylindrical configuration with its outermost edge being spaced longitudinally inwardly thereof in general alignment with the innermost portion of said retaining bumps for engagement by said circular flange portion of said holder after the edge thereof has been snapped over said retaining bumps during assembly of said overcap onto aid one end of said holder whereby to limit inward movement of said holder into said overcap so as to prevent engagement of said hardened medicated matrix affixed to said one end of said holder with said closed end of said tubular overcap.

12. The invention as defined in claim 9 wherein the medication in said medicated hardened matrix affixed to said one end of said one-piece elongated molded plastic holder is fentanyl citrate.

* * * * *